(12) United States Patent
Ries (10) Patent No.: US 10,390,968 B2
(45) Date of Patent: Aug. 27, 2019

(54) DEVICE FOR SPINAL SURGERY, CORRESPONDING GUIDE SLEEVE AND KIT WITH GUIDE SLEEVE

(71) Applicant: JOIMAX GMBH, Karlsruhe (DE)

(72) Inventor: Wolfgang Ries, Linkenheim-Hochstetten (DE)

(73) Assignee: JOIMAX GMBH, Karlsruhe (DE)

( * ) Notice: Subject to any disclaimer, the term of this patent is extended or adjusted under 35 U.S.C. 154(b) by 0 days.

(21) Appl. No.: 15/761,625

(22) PCT Filed: Aug. 4, 2016

(86) PCT No.: PCT/EP2016/001342
§ 371 (c)(1),
(2) Date: Mar. 20, 2018

(87) PCT Pub. No.: WO2017/050410
PCT Pub. Date: Mar. 30, 2017

(65) Prior Publication Data
US 2018/0344480 A1    Dec. 6, 2018

(30) Foreign Application Priority Data
Sep. 23, 2015   (DE) .......................... 10 2015 012 171

(51) Int. Cl.
*A61F 2/46* (2006.01)
*A61F 2/44* (2006.01)
(Continued)

(52) U.S. Cl.
CPC ............ *A61F 2/4611* (2013.01); *A61F 2/447* (2013.01); *A61B 2017/0256* (2013.01); *A61F 2002/30125* (2013.01); *A61F 2002/4687* (2013.01)

(58) Field of Classification Search
CPC ................... A61F 2/4611; A61F 2/447; A61F 2002/30125; A61F 2002/4687; A61B 2017/0256
(Continued)

(56) References Cited

U.S. PATENT DOCUMENTS 7,033,362 B2    4/2006  McGahan et al.
8,062,299 B2    11/2011 McGahan et al.
(Continued)

FOREIGN PATENT DOCUMENTS

DE         601 04 286 T2      7/2005
DE         20 2013 007361 U1  3/2014
DE         20 2014 003441 U1  11/2014

*Primary Examiner* — Pedro Philogene
*Assistant Examiner* — David C Comstock
(74) *Attorney, Agent, or Firm* — McGlew and Tuttle, P.C.

(57) ABSTRACT

To reduce the stress of a patient as much as possible during a percutaneous spine surgery for inserting an interbody cage between two vertebrae, between which the intervertebral disk was damaged and was therefore removed, a guide sleeve is provided for the spine surgery, which is characterized by a non-cylindrical jacket. A kit is further provided for spine surgery with at least one guide sleeve of the above-mentioned type and a dilator, having an outer contour that is adapted to the contour of the lumen of the guide sleeve. A kit for spine surgery is further provided including a guide sleeve and an interbody cage, which is to be inserted through this guide sleeve. The lumen of the guide sleeve is adapted to a maximum cross-sectional contour of the interbody cage.

24 Claims, 7 Drawing Sheets

(51) Int. Cl.
*A61B 17/02* (2006.01)
*A61F 2/30* (2006.01)

(58) Field of Classification Search
USPC .................................. 606/99, 86 A; 600/208
See application file for complete search history.

(56) References Cited

U.S. PATENT DOCUMENTS

| | | |
|---|---|---|
| 2004/0097932 A1 | 5/2004 | Ray, III et al. |
| 2005/0119747 A1 | 6/2005 | Fabris Monterumici et al. |
| 2006/0247654 A1 | 11/2006 | Berry |
| 2007/0073399 A1 | 3/2007 | Zipnick et al. |
| 2008/0221586 A1* | 9/2008 | Garcia-Bengochea ..................... A61B 17/02 606/108 |
| 2008/0255563 A1 | 10/2008 | Farr et al. |
| 2012/0130161 A1 | 5/2012 | Lauryssen et al. |
| 2012/0330417 A1 | 12/2012 | Zipnick |
| 2015/0250612 A1 | 9/2015 | Schifano et al. |

* cited by examiner

DEVICE FOR SPINAL SURGERY, CORRESPONDING GUIDE SLEEVE AND KIT WITH GUIDE SLEEVE

CROSS REFERENCE TO RELATED APPLICATIONS

This application is a United States National Phase Application of International Application PCT/EP2016/001342, filed Aug. 4, 2016, and claims the benefit of priority under 35 U.S.C. § 119 of German Application 10 2015 012171.5, filed Sep. 23, 2015, the entire contents of which are incorporated herein by reference.

FIELD OF THE INVENTION

The pertains to a device for spinal surgery, with at least one guide sleeve, with at least one dilator, whose outer contour corresponds to the inner contour of the guide sleeve, as well as to an insertion kit for spinal surgery. The present invention pertains, furthermore, to a corresponding guide sleeve for spinal surgery, especially as a part of a kit and to a kit for spinal surgery, comprising a guide sleeve and an interbody cage for spinal surgery, which said cage is to be placed through said guide sleeve, with such a guide sleeve and with at least one dilator, as well as to a kit comprising a guide sleeve and an interbody cage to be inserted into an intervertebral area.

BACKGROUND OF THE INVENTION

More and more conventional procedures, in which the spine is exposed in the area in which the surgery is to be performed by considerable incisions in the back of the patient and by cutting through muscles, are replaced in spinal surgery by percutaneous spinal surgery. To make it possible to find ways for inserting instruments through the skin as well as through tissues located in front of the spine and the vertebrae as well as to make it possible to work percutaneously with such devices, a guide sleeve or working sleeve having a sufficient lumen and hence a sufficient cross section is inserted. This cannot be easily inserted as such. The skin and the subjacent tissue is rather pierced first with a thin needle kit comprising a stylet and a hollow needle narrowly surrounding same, both of which taper distally, i.e., are pointed (Jamshidi needle). The stylet is then removed from the hollow needle, and a guide wire is passed through the hollow needle to the intervertebral disk space or intervertebral foramen. The hollow needle is then removed and a first dilator is inserted via the guide wire. Additional dilators, which are closely adapted with their lumen to the outer contour of the dilator inserted previously, are inserted via this dilator. The dilators are tapered conically at their ends. This is carried out until the guide sleeve or working sleeve can then be inserted via a last dilator, and the guide wire and the dilators are then removed from this guide sleeve or working sleeve, and the surgeon can then perform the procedure through the lumen by inserting instruments, etc., and via these instruments or by inserting an intervertebral cage (interbody cage) into the intervertebral foramen. All the above-mentioned steps as well as the further steps are carried out under X-ray monitoring.

The dilators and especially the working sleeve or guide sleeve have hitherto regularly been made with a cylindrical configuration. It was found that especially when inserting an interbody cage, the stress of the patient, which is substantially reduced by the percutaneous procedure only compared to an open surgery, is still undesirable, because especially the lateral cross-sectional dimensions of a cage are rather large and the diameter of a conventional cylindrical guide sleeve must still therefore likewise be rather large as well.

SUMMARY OF THE INVENTION

A basic object of the present invention is therefore to provide a device and a guide sleeve for spinal surgery as well as a kit comprising a guide sleeve and intervertebral bodies, with the use of which the stress of the patient can be substantially reduced further during a percutaneous spinal surgery.

This object is accomplished according to the present invention first with a device for spinal surgery of the type mentioned in the introduction, which is characterized by a non-cylindrical jacket a jacket with a non-circular cross section, such as a jacket with a tubular configuration with one or more non-curved sides or with curved sides not forming a circular cross section.

To accomplish this object, the present invention provides, furthermore, a guide sleeve, which is characterized by a non-cylindrical jacket. A spinal surgery kit comprising a guide sleeve and interbody cages, which are to be inserted and to be placed through said guide sleeve, is also provided for accomplishing the object, said kit being characterized in that the lumen of the guide sleeve is adapted to the maximum cross-sectional contour of the interbody cage.

The device according to the present invention, which is also used as an insertion kit, accordingly has at least one guide sleeve configured in the aforementioned shape as well as at least one—first or outermost—dilator (which is, however, nevertheless arranged within the guide sleeve and via which the guide sleeve is inserted), whose outer contour is adapted to the inner lumen of the guide sleeve.

It is achieved due to the configuration according to the present invention of the device and of the guide sleeve itself as well as of the implantation kit containing same that the stress of a patient, in whom a percutaneous procedure, especially the insertion of an interbody cage, is performed through such a guide sleeve, is substantially reduced, because the height of the guide sleeve is markedly reduced compared to conventional cylindrical guide sleeves, so that there is a markedly reduced dilation and hence precisely a reduced risk of compression for the exiting nerve roots.

In a preferred variant, the present invention makes provisions in the guide sleeve for two mutually broad sides having a breadth that is greater than the breadth of narrow sides connecting these. This applies especially if this is small at the level of the intervertebral disk space. Furthermore, one of the broad sides may be flat and/or one of the broad sides may be bent convexly outwards, having now especially a radius of curvature of 11 mm to 12.5 mm. Moreover, the present invention makes provisions in a preferred embodiment for the bend angle of the transition between a broad side and a narrow side to be between 3 mm and 4.5 mm.

Provisions are made according to an extremely preferred variant of the present invention for the narrow sides of the guide sleeve to have distally the projections projecting over the broad sides, with the projections tapering, in particular, towards their free ends and being rounded at their free ends, and for the narrow sides to have a greater thickness than the broad sides, the thickness of the broad sides preferably being 0.8 mm to 1.2 mm and/or the thickness of the narrow sides being greater than 1.2 mm to 1.7 mm.

Provisions are made, in particular, in a variant of the insertion kit comprising a guide sleeve and a dilator adapted to same in its outer contour for the lumen of the dilator to have a cylindrical configuration. It is achieved hereby that the additional inner dilators, which are inserted first over the guide wire that is already in place or one over another through the skin and tissue to the site of the procedure to be performed on the spine, may, furthermore, be configured in the known manner with cylindrical contour, without this leading to an increased stress for the patient and without the reduced stress achieved through the embodiment according to the present invention of the guide sleeve and of the last dilator, via which the guide sleeve is directly inserted, being compromised.

Provisions are made in another preferred embodiment for the sleeve and/or the dilator to have grooves extending at right angles to its longitudinal axis in the proximal area of its outer side, especially on its narrow sides. These grooves are used to guarantee a better grip for fingers or for a tool for extracting the sleeve or the dilator. Provisions are made in a variant for openings located diametrically opposite to be present in the proximal tooth/wedge area.

Finally, provisions are made in the implantation kit for spine surgery comprising a guide sleeve and interbody cage for the guide sleeve to be preferably configured corresponding to one or more of the above-described embodiments.

Figure 7:
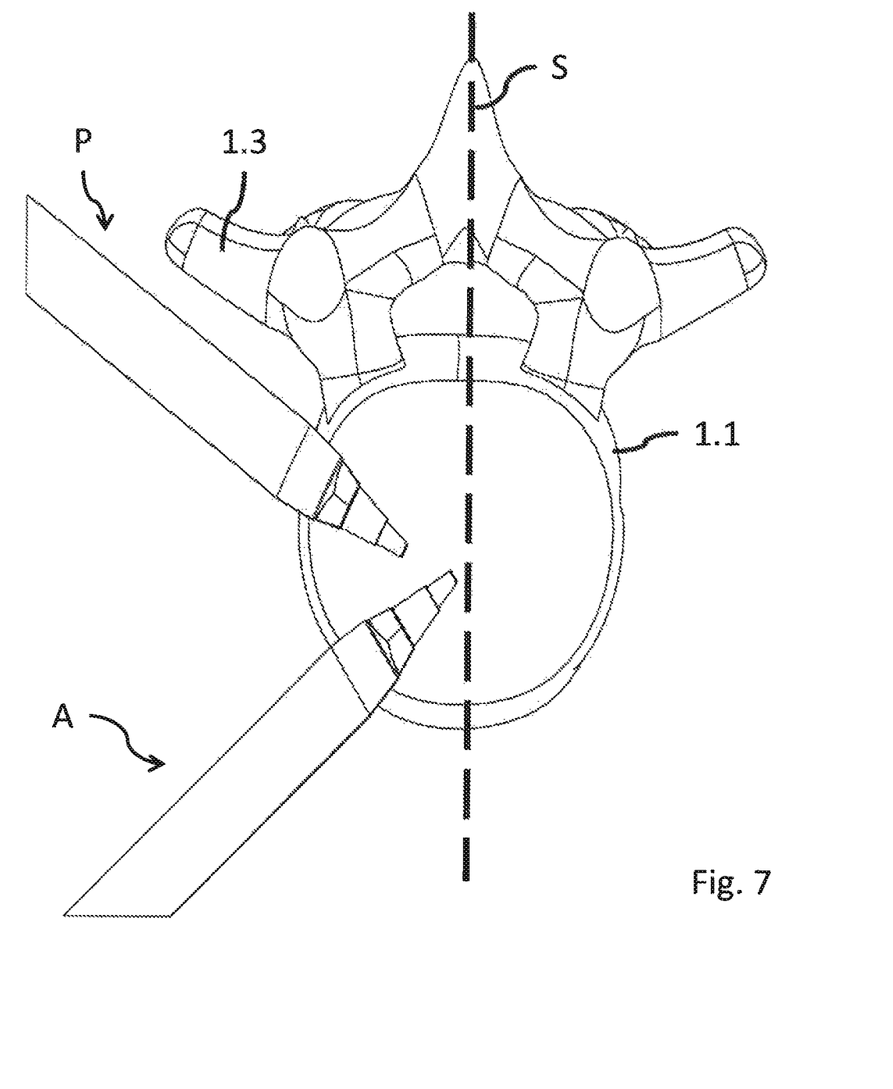
FIG. 7 is a view to the alternative posterolateral access or anterolateral access to the intervertebral disk space.

The access to the intermediate space (intervertebral disk space) between two vertebrae by means of the device according to the present invention is possible both posterolaterally and anterolaterally, preferably with an access angle of 30° to 60° and preferably 40° to 50° each, both relative to the—central—sagittal plane or along a—horizontal—sagittal axis located in that plane, at the top in the rear or in the front from the side, as this is shown in FIG. 7. The posterolateral access may preferably be along the outer lateral surface of the processus spinosus.

Further advantages and features of the present invention appear from the claims, from the following description, in which an exemplary embodiment of the present invention is explained in detail with reference to the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1.1 is a lateral view of a guide sleeve of the device according to the present invention with distal projections protruding into the intervertebral disk space between two vertebrae;

FIG. 1.2 is an end face of the guide sleeve according to FIG. 1 with an interbody cage inserted;

FIG. 1.3 is a perspective view of the embodiment according to FIG. 1 with an interbody cage inserted into the guide sleeve at the proximal end;

FIG. 4.1 is a perspective view of a guide sleeve, viewed obliquely from its distal end;

FIG. 4.2 is a lateral view of the guide sleeve according to FIG. 6.1;

FIG. 5.1 is a perspective view of a non-cylindrical dilator of a device according to the present invention, which dilator is used directly within the guide sleeve;

FIG. 5.2 is a lateral view of the dilator according to FIG. 5.1;

FIG. 6.1 is a top view of the device according to the present invention with a guide sleeve in the kit with two dilators inserted into this guide;

FIG. 6.2 is a lateral view of the device of FIG. 6.1 with the guide sleeve in the kit with two dilators inserted into this guide;

FIG. 6.3 is a perspective view from the proximal end of the device of FIG. 6.1 with the guide sleeve in the kit with two dilators inserted into this guide;

FIG. 6.4 is a perspective view towards the distal end of the device of FIG. 6.1 with the guide sleeve in the kit with two dilators inserted into this guide;

FIG. 6.5 is an enlarged view of the distal end of the kit according to FIGS. 6.1 through 6.4.

DESCRIPTION OF THE PREFERRED EMBODIMENTS

Referring to the drawings, In case of injuries to intervertebral disks, in which these must be partially and especially completely removed, at least one interbody cage 2 is to be inserted between the vertebrae 1.1, 1.2 located adjacent to the affected intervertebral disk to stabilize the spine.

An interbody cage 2 may have different contours. A cage 2 as is shown, for example, in FIG. 2 in a perspective view proved to be suitable. Such a cage has a stable outer frame 2.1 and an inner, porous, grid-like or net-like structure 2.2, which enables the bone of the adjacent vertebrae 1.1, 1.2 to grow into this structure in order thus to establish a firm connection.

Figure 2:
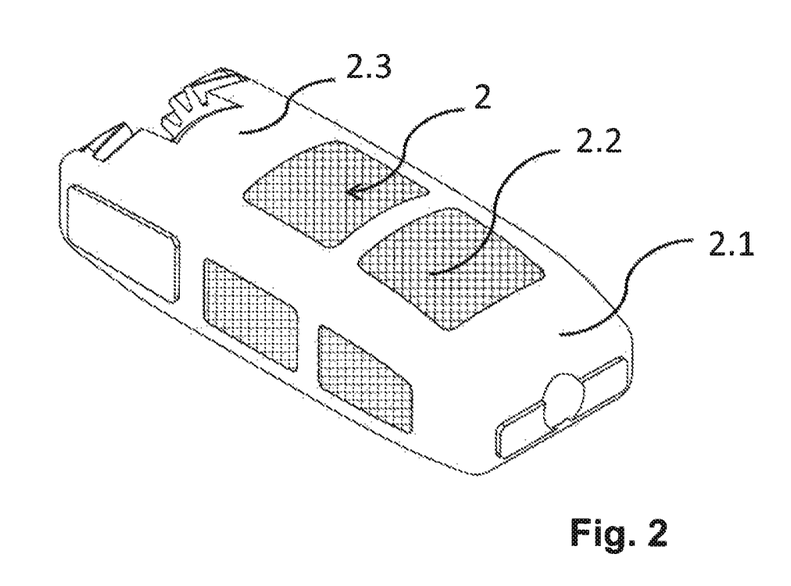
FIG. 2 is a schematic view of a typical interbody cage in a perspective view.

As is seen, the cage tapers in the longitudinal direction towards its distal end. The upper surface 2.3 is bent over the width convexly with a relatively large radius of curvature. This makes it possible to adapt the relative positions of the vertebrae over the cage 2. By contrast, the lower surface of the cage, just like the side walls, does not have an arc-shaped configuration over its breadth or height but has an at least nearly flat configuration.

Figure 11:
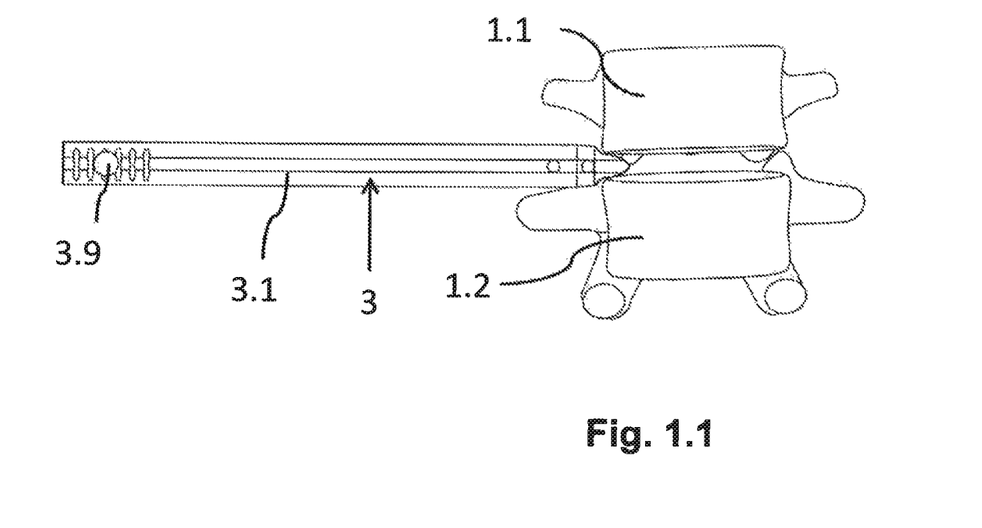
Figure 12:
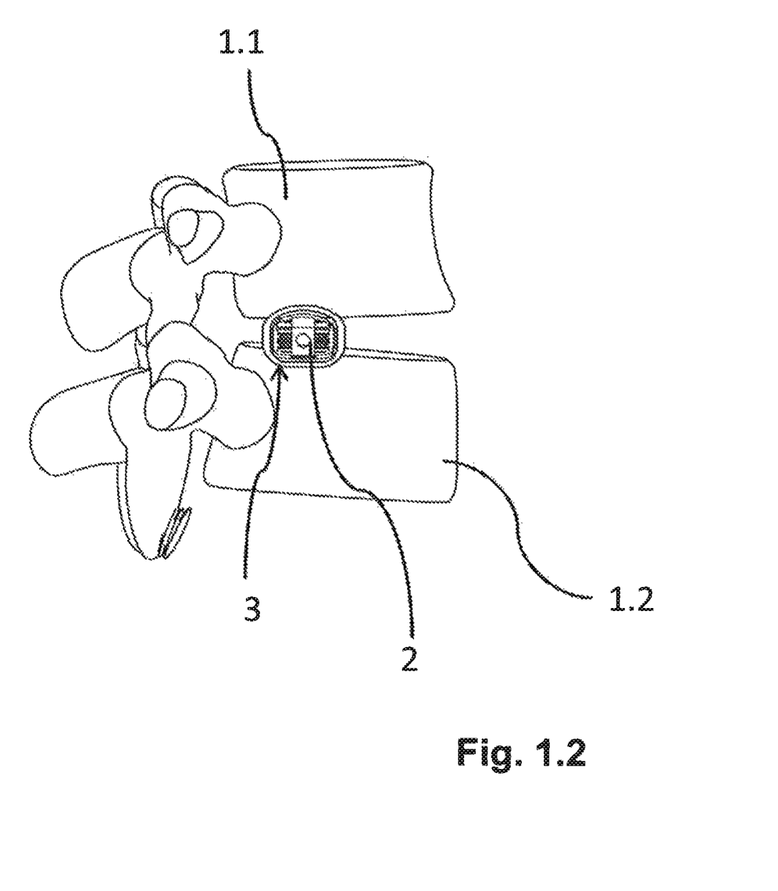
Figure 13:
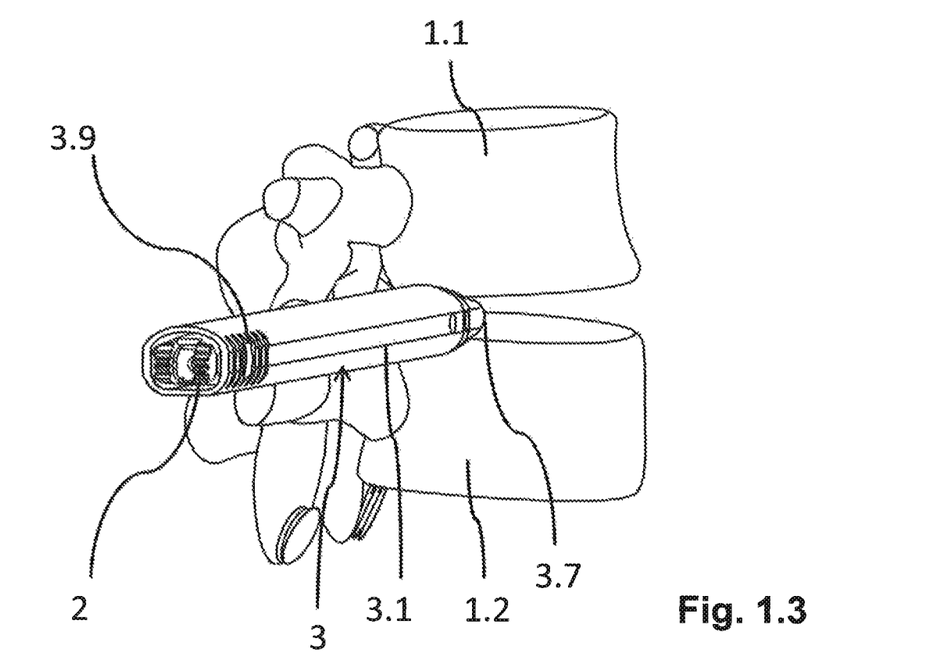

As this can be see in FIGS. 1.1 through 1.3, such an interbody cage is inserted through a guide sleeve 3 into the intervertebral area or the former intervertebral disk space.

Figure 3:
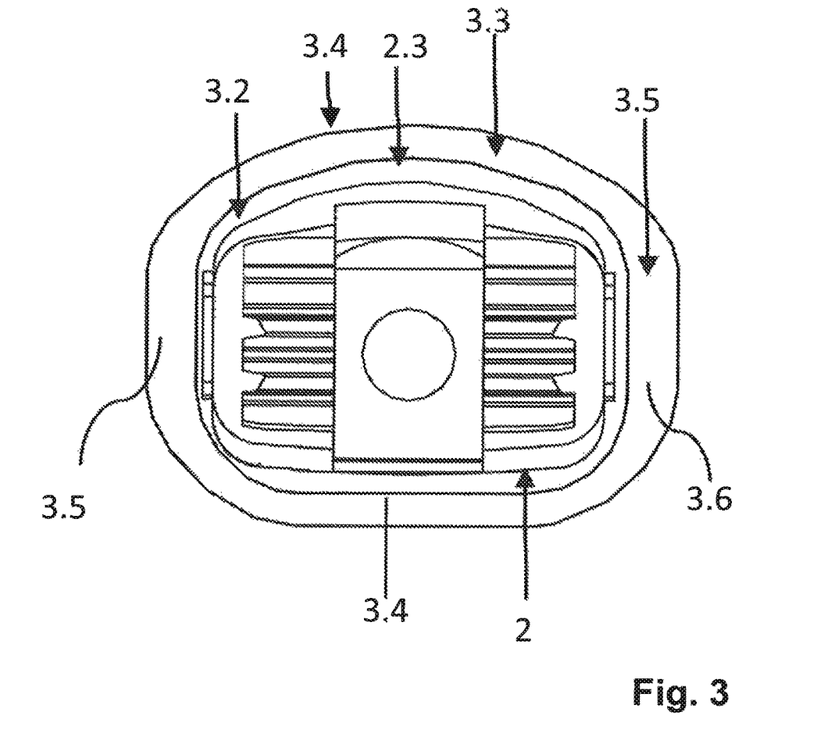
FIG. 3 is a top view of the proximal end of a guide sleeve with a cage inserted.

As can be seen especially also in FIGS. 3 through 4.2, the guide sleeve 3 has a non-cylindrical jacket 3.1 over an entire jacket length and an (inner) lumen 3.2 with a non-cylindrical, constant lumen cross section. The cross-sectional contour of the lumen 3.2 of the guide sleeve 3 is adapted to the maximum cross-sectional contour of the interbody cage 2 (FIG. 2) to be inserted, i.e., to the cross-sectional contour thereof at a short distance in front of the proximal end of the cage 2 with sufficient tolerance.

The jacket 3.1 and the wall of the guide sleeve 3 have essentially mutually opposite upper and lower broad sides 3.3, 3.4 as well as narrow sides 3.5, 3.6 connecting those, namely, two mutually opposite narrow sides 3.5, 3.6 in this exemplary embodiment.

The lower broad side 3.4 essentially has, just like the narrow sides 3.5, 3.6, a flat configuration on the inner side towards the lumen, and the transition between the broad side 3.4 and the narrow sides 3.5, 3.6 does not have sharp angles, but is rounded, the radius of curvature of the transition between the lower broad side 3.4 and the narrow sides 3.5, 3.6 being 4 mm here.

The upper broad side 3.3 has an outwardly convexly bent configuration (i.e., it is not flat) over the breadth of the guide sleeve 3. The radius of curvature of the upper broad side is 12 mm here. The sleeve has transverse grooves 3.8 on its proximal outer side as well as diametrically opposite wall openings 3.9. The grip for fingers of the surgeon or tools is improved by this configuration.

Figure 41:
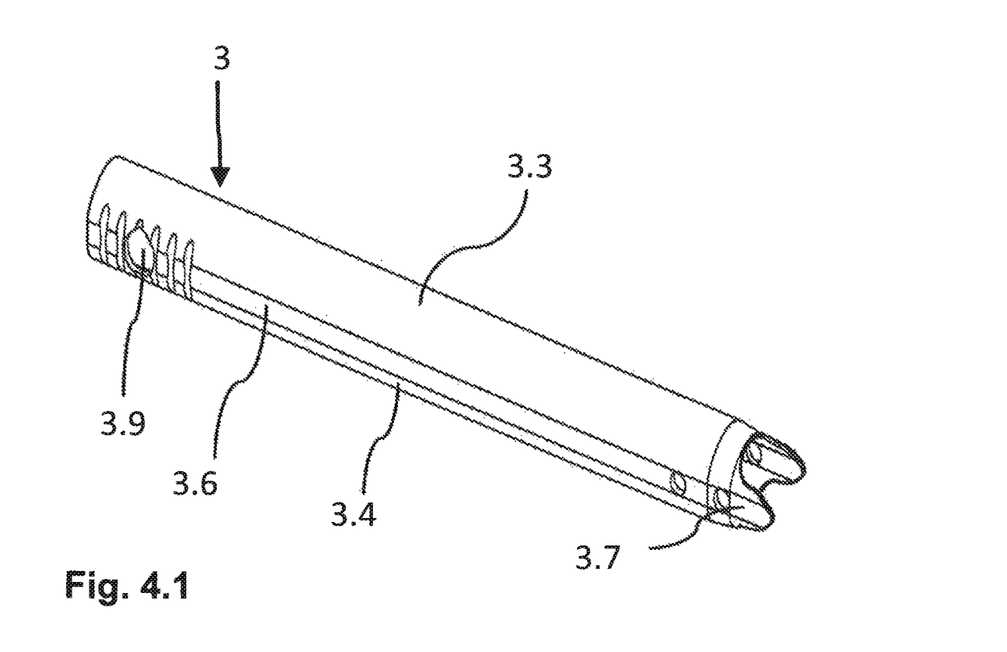
Figure 42:
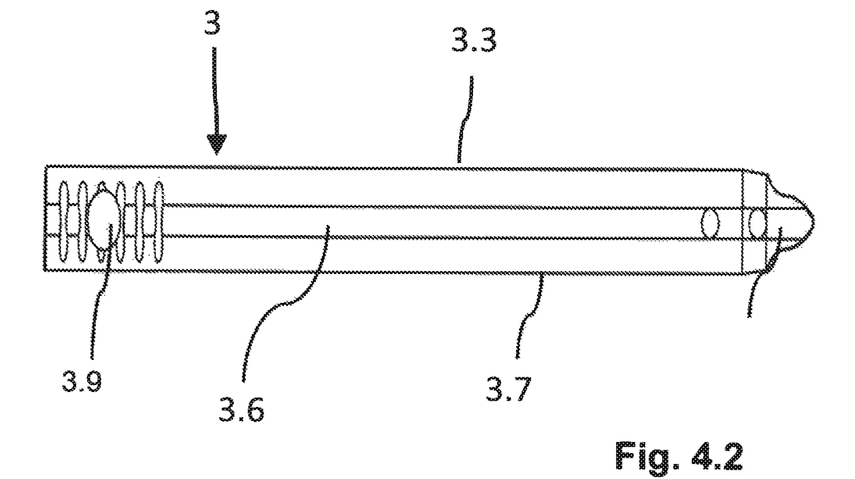

As can likewise be seen especially in FIG. 3, the wall thickness of the upper and lower broad sides 3.3, 3.4 is smaller than the wall thickness of the narrow sides 3.5, 3.6. While the wall thickness of the upper and lower broad sides 3.3, 3.4 is typically approx. 1 mm in the exemplary embodiment shown, the wall thickness of the narrow sides 3.5, 3.6 is approx. 1.5 mm (the view in FIG. 3 is an enlarged view). Projections 3.7, which are distal projections, are formed at the distal end of the narrow sides 3.5, 3.6 (FIGS. 1, 4.1 through 4.5). These are used, on the one hand, for a firm anchoring of the guide sleeve between the two vertebrae 1.1 and 1.2 and, on the other hand, also for dilating the intermediate space, so that the cage 2 can be inserted between the two vertebrae 1.1, 1.2. Since the projections 3.7 form an extension of the narrow sides 3.5, 3.6, higher stability is imparted by the greater wall thickness of the narrow sides 3.5, 3.6 on the projections 3.7, so that these can fulfill their task of securely anchoring the guide sleeve 3 and dilating the intermediate space between the vertebrae 1.1, 1.3 with certainty.

The interbody cage 2 and the guide sleeve 3 together form a kit for spinal surgery. Their cross-sectional contour, the outer contour of the cage 2 and that of the lumen of the guide sleeve 3, are adapted to one another.

Figure 51:
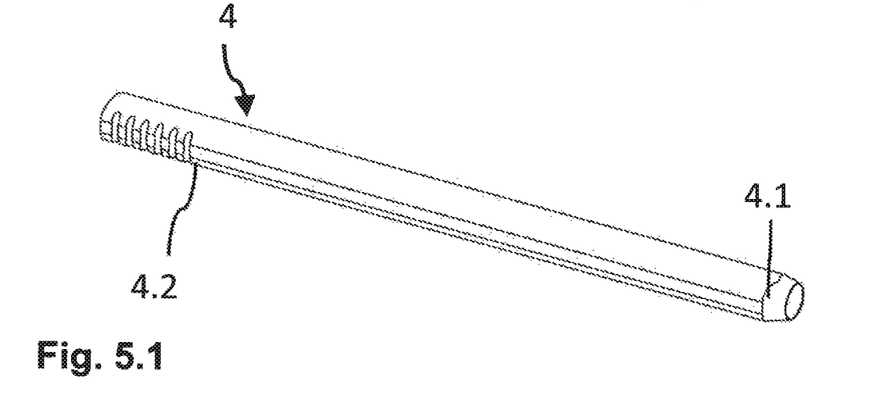
Figure 52:
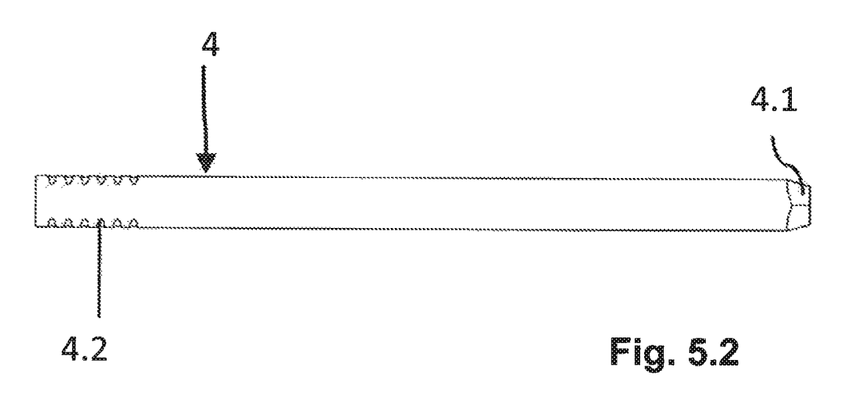
Figure 61:
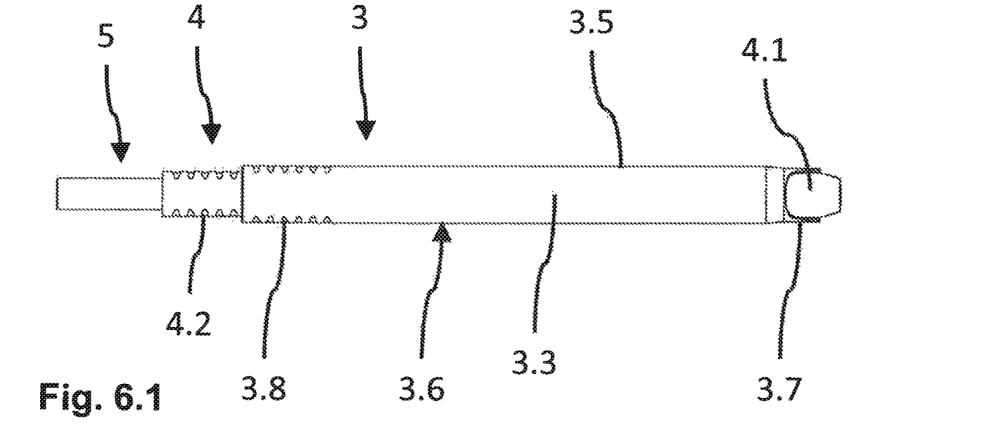
Figure 62:
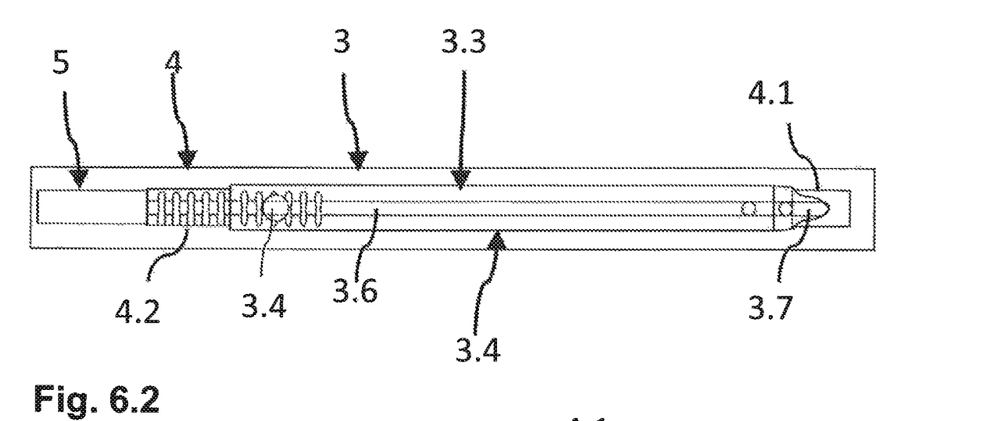

FIGS. 5.1 and 5.2 show a dilator 4, which comes to lie directly within the guide sleeve 3 when the latter is pushed over it. The outer contour of the dilator 4 located directly within the guide sleeve 3 is accordingly adapted to the lumen of the guide sleeve 3 with narrow tolerances. This means that the lower outer broad side of the dilator, just as the outer narrow sides thereof, have a largely flat configuration, while the upper outer broad side is bent convexly outwards. The outer cross-sectional contour of the dilator 4 is constant over the largest part of its length; only the distal end 4.1 of the dilator 4 tapers conically, as is common in case of such dilators.

Figure 63:
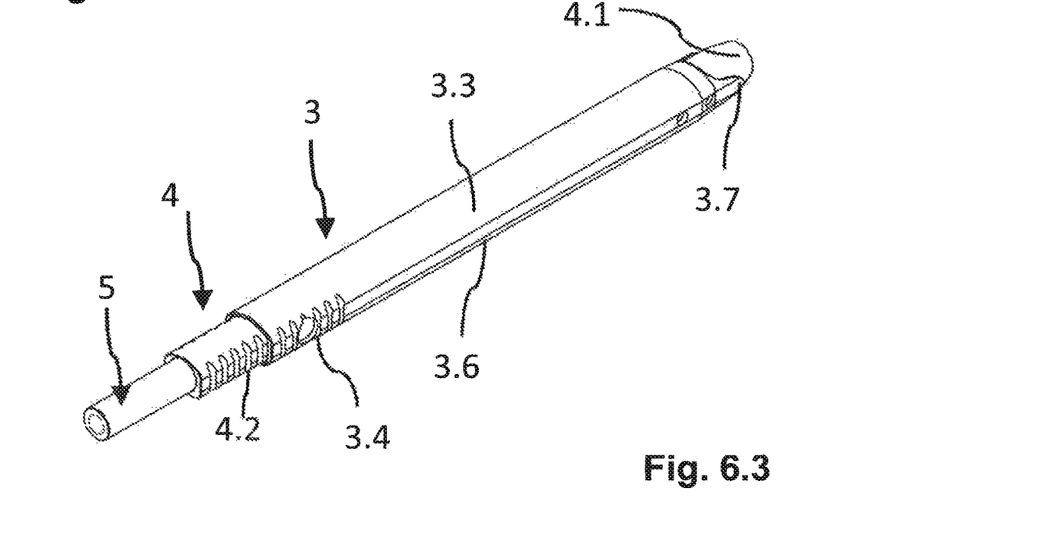
Figure 64:
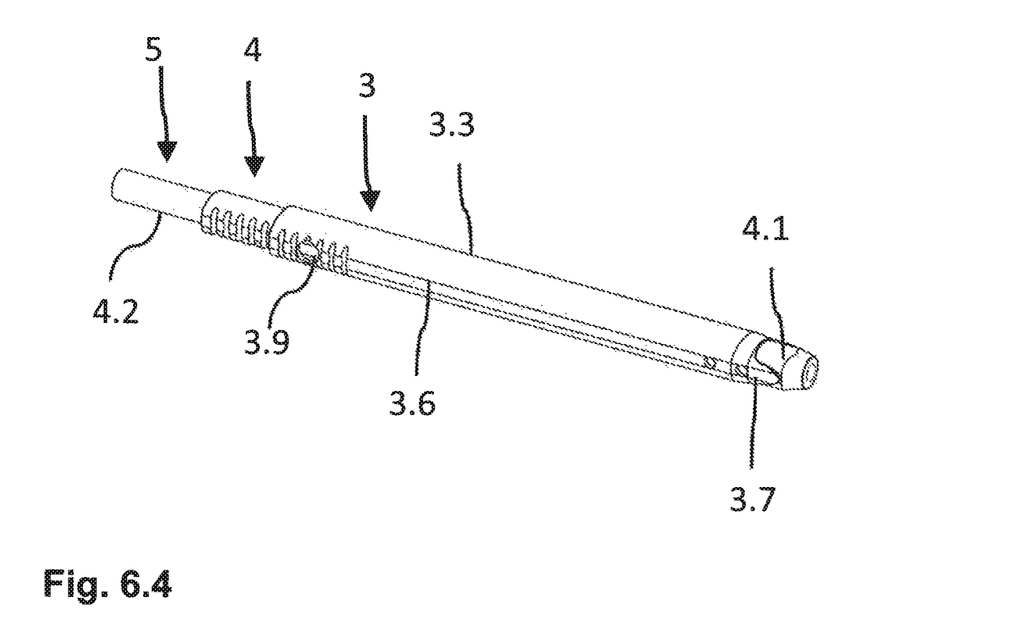
Figure 65:
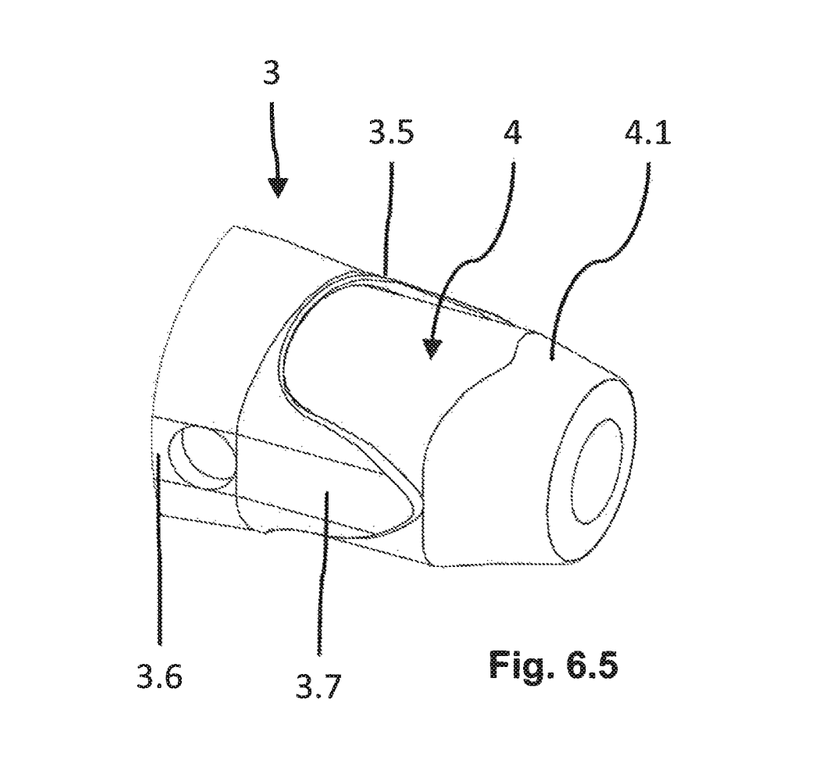

As can be seen in FIG. 5.1 especially at the right—distal—end of the dilator 4, in or also at the left—proximal—end in FIG. 6.3, the inner lumen of the dilator 4 is cylindrical, i.e., the proximal and distal inlet and outlet openings are circular. The dilator 4 also has transverse grooves 4.3 on its proximal outer side.

FIGS. 6.1 through 6.5 show an (insertion) kit for spinal surgery with a guide sleeve, as was described above, and with two dilators shown, namely, the dilator 4 described above especially with reference to FIGS. 5.1 and 5.2 and another dilator 5, which comes to lie within the dilator 4 or is pushed over the dilator 4.

The additional dilator 5 shown in FIGS. 6.1 through 6.5, which is located on the inside, has, correspondingly to the cylindrical inner contour of the dilator 4, a cylindrical outer contour and—likewise also a cylindrical inner contour —, as this is common in such dilators. The two individual kits comprising the parts 2, 3, on the one hand, and 3, 4, 5, on the other hand, form a common surgical kit.

The access to the intermediate space (intervertebral disk space) between two vertebrae 1.1, 1.2 by means of the device according to the present invention is possible both posterolaterally P and anterolaterally A, preferably with an access angle of 30° to 60° each and preferably 40° to 50°, always in relation to the—central—sagittal plane S or in the—horizontal—sagittal axis located in this plane at the top in the rear or in the front from the side, as this is shown in FIG. 7. The posterolateral access may be preferably along the outer lateral surface of the processus spinosus 1.3 of the vertebra 1.1.

It is achieved due to the non-cylindrical configuration according to the present invention of the guide sleeve according to the present invention that, on the one hand, even though an interbody cage can be inserted through it, the stress on the tissues of a patient in the area in which the guide sleeve 3 is inserted between the skin surface and the intervertebral disk space, especially in the direction in which the spine extends, is stressed, on the other hand, as little as possible, because the height of the guide sleeve can be substantially reduced due to the configuration of the guide sleeve according to the present invention compared to conventional cylindrical guide sleeves (with a circular cross section).

While specific embodiments of the invention have been shown and described in detail to illustrate the application of the principles of the invention, it will be understood that the invention may be embodied otherwise without departing from such principles.

The invention claimed is:

1. A guide sleeve, for spinal surgery that forms a part of a kit, the guide sleeve comprising a non-cylindrical jacket, the non-cylindrical jacket comprising narrow sides and two broad sides, the two broad sides being opposite each other, the two broad sides having a width greater than a width of the narrow sides, one of the broad sides being flat, another one of the broad sides being convexly bent outwards, wherein a radius of curvature of a transition between one of the broad sides and one of the narrow sides is between 3 mm and 4.5 mm.

2. A guide sleeve in accordance with claim 1, wherein the another one of the broad sides is bent convexly outwards with a bend angle of 11 mm to 12.5 mm.

3. A guide sleeve in accordance with claim 1, wherein the narrow sides distally have projections projecting over the broad sides, the one of the broad sides comprising a planar, non-curved outer surface of the non-cylindrical jacket.

4. A guide sleeve in accordance with claim 3, wherein the projections taper to their free end and are rounded at the free end.

5. A guide sleeve in accordance with claim 1, wherein the narrow sides have a greater thickness than the broad sides, the thickness of the broad sides being 0.8 mm to 1.2 mm or the thickness of the narrow sides being greater than 1.2 mm to 1.7 mm or both the thickness of the broad sides being 0.8 mm to 1.2 mm and the thickness of the narrow sides being greater than 1.2 mm to 1.7 mm.

6. A guide sleeve in accordance with claim 1, wherein the sleeve has grooves extending at right angles to a longitudinal axis in a proximal area of an outer side thereof, on the narrow side of the sleeve.

7. A guide sleeve in accordance with claim 1, wherein the guide sleeve has openings located diametrically opposite in a proximal area.

8. A device for spine surgery, the device comprising:
    at least one guide sleeve; and
    at least one dilator having an outer contour that corresponds to the inner contour of the at least one guide sleeve, wherein the guide sleeve has a non-cylindrical jacket, the non-cylindrical jacket comprising narrow sides and two broad sides, the two broad sides being opposite each other, the two broad sides having a width greater than a width of the narrow sides, one of the broad sides being flat, another one of the broad sides being convexly bent outwards, wherein a radius of curvature of a transition between one of the broad sides and one of the narrow sides is between 3 mm and 4.5 mm.

9. A device in accordance with claim 8, wherein the another one of the broad sides has a radius of curvature of 11 mm to 12.5 mm.

10. A device in accordance with claim 8, wherein the narrow sides have distally directed projections projecting over the broad sides, the one of the broad sides comprising a planar, non-curved outer surface of the non-cylindrical jacket.

11. A device in accordance with claim 10, wherein the projections are tapered towards a free end thereof and are round at the free end.

12. A device in accordance with claim 8, wherein the narrow sides have a greater thickness than the broad sides, the thickness of the broad sides being 0.8 mm to 1.2 mm and/or the thickness of the narrow sides being greater than 1.2 mm to 1.7 mm.

13. A device in accordance with claim 8, wherein the sleeve has grooves extending at right angles to a sleeve longitudinal axis in a proximal area of one of the narrow sides of the sleeve.

14. A device in accordance with claim 8, wherein openings are located diametrically opposite in a device proximal area.

15. A device according to claim 8, wherein a lumen of the dilator has a cylindrical configuration.

16. A device according to claim 8, wherein the dilator has grooves extending at right angles to a dilator longitudinal axis in a proximal area of an outer side.

17. A spine surgery kit comprising:
 a guide sleeve comprising a non-cylindrical jacket, the non-cylindrical jacket comprising narrow sides and two broad sides, the two broad sides being opposite each other, the two broad sides having a width greater than a width of the narrow sides, one of the broad sides being flat, another one of the broad sides being convexly bent outwards, wherein a radius of curvature of a transition between one of the broad sides and one of the narrow sides is between 3 mm and 4.5 mm; and
 an interbody cage to be placed through the guide sleeve, wherein a lumen of the guide sleeve is adapted to a maximum cross-sectional contour of the interbody cage.

18. A spine surgery kit in accordance with claim 17, further comprising at least one dilator having an outer contour that corresponds to an inner contour of the at least one guide sleeve, wherein the guide sleeve has a non-cylindrical jacket.

19. A spine surgery kit in accordance with claim 17, wherein the another one of the broad sides has a radius of curvature of 11 mm to 12.5 mm.

20. A spine surgery kit in accordance with claim 17, wherein the one of the broad sides comprises a planar, non-curved outer surface of the non-cylindrical jacket.

21. A spine surgery kit in accordance with claim 20, wherein the projections are tapered towards a free end thereof and are round at the free end.

22. A spine surgery kit in accordance with claim 20, wherein the narrow sides have a greater thickness than the broad sides, the thickness of the broad sides being 0.8 mm to 1.2 mm and/or the thickness of the narrow sides being greater than 1.2 mm to 1.7 mm.

23. A spine surgery kit in accordance with claim 17, wherein the sleeve has grooves extending at right angles to a sleeve longitudinal axis in a proximal area of one of the narrow sides of the sleeve.

24. A spine surgery kit in accordance with claim 17, wherein openings are located diametrically opposite in a device proximal area.

\* \* \* \* \*